March 2, 1971 R. H. McCOLLEY Plant Pat. 3,034
PHILODENDRON PLANT
Filed March 10, 1969
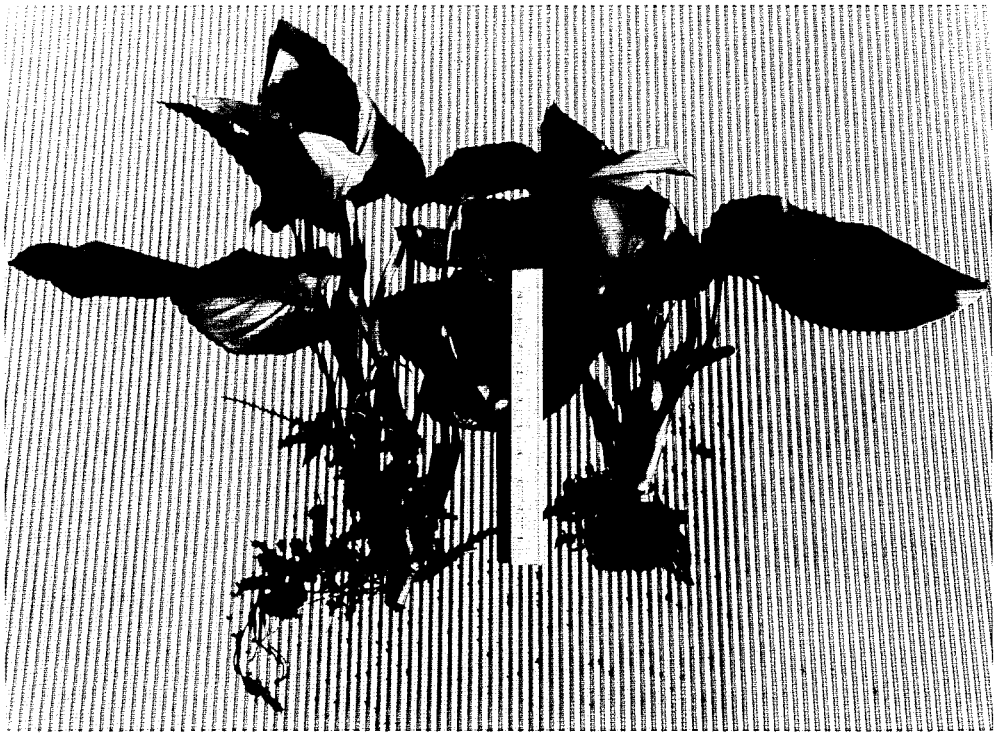
Inventor:
R. H. McColley
Robb & Robb
Attorneys

United States Patent Office

Plant Pat. 3,034
Patented Mar. 2, 1971

3,034

PHILODENDRON PLANT

Robert H. McColley, Orlando, Fla., assignor to Yoder Bros. Inc., Barberton, Ohio

Filed Mar. 10, 1969, Ser. No. 805,911
Int. Cl. A01h *5/00*
U.S. Cl. Plt.—88 1 Claim

My present invention comprises a new and distinct variety of philodendron plant, the result of crossing several unpatented and unnamed varieties of my own origination which I do not otherwise designate, but which were in turn bred and selected by me from previous crosses made during the course of an extensive program of hybridizing.

Actually the female parent of the instant variety was in turn bred from an unnamed seedling resulting from a cross between the two species, *Philodendron hastatum* and *Philodendron erubescens.*

The male parent as indicated was also bred and selected by me and it was in turn an unnamed seedling whose female parent was (*Philodendron hastatum* × *Philodendron erubescens*) × *Philodendron wendlandii,* and whose male parent was *Philodendron imbe.* There are therefore four distinct philodendron species utilized in the hybridization of the instant new variety.

My present new variety is essentially the result of an extensive hybridizing program which has been carried on for many years in my greenhouses in Orlando, Fla., and has involved the selection of characteristics of certain parental varieties which I believe were valuable and which were in turn in most cases of my own origination developed from the various philodendron species known.

The result of the specific hybridization outlined in detail hereinbefore has been to produce the present new and distinct variety, to in turn provide for a fast rate of growth as indicated by the fact that under normal greenhouse conditions a young plant may be developed in three months from a tip cutting. While it requires six months to produce a mature plant from the same type of cutting, this is in turn indicative of the relatively fast rate of growth provided by my new variety.

My new variety is vigorous, compact and non-branching and an average plant of five leaves propagated from tip cuttings attains a height of 10 inches with a spread of 15 to 18 inches. A five-leaved plant propagated from single eye cuttings may attain a height of 8 inches with a spread of 9 to 12 inches.

My instant new variety is a foliage plant as is usually true of philodendrons, but it is distinctly different from both of its parents or any other philodendron presently known to me.

It may be contrasted with prior known varieties and particularly those which I have grown myself, by pointing out that in contrast to Burgundy, the instant new variety elongates at about half the rate, staying short longer with an overall smaller leaf.

My instant new variety produces longer leaves with shorter petioles in contrast to Burgundy, in which the leaves are too large and too open.

Better plant volume is provided by my new variety among other things, but one of the important improvements of my instant new variety is its very resistance to bacterial soft rot and good resistance to "shotgun fungus."

My new variety has been asexually reproduced by tip cuttings in the vicinity of Orlando, Fla., and has also been asexually reproduced by single eye cuttings in the same vicinity, observations having been made of the leaf, stem and petiole color characteristics under daylight illumination under clear vinyl of not more than 30% light reduction (Bailey, L. H. and Bailey, E. Z. Hortus Second 1949).

My new variety has been found to retain its distinctive characteristics through successive asexual reproductions.

The accompanying drawing forming a part hereof shows a typical plant of my new variety, the colors being as nearly representative of the actual colors of the plant as is possible in such an illustration.

The color references are made based upon comparison with the Munsell Book of Color, 1963 edition.

DESCRIPTION

Leaf form characteristics:

*Shape.*—Immature leaf—Ovate, mature leaf—Ovate.
*Tip.*—Acuminate.
*Base.*—Immature leaf—obtuse, mature leaf—auriculate.
*Leaf attachment.*—Stalked.
*Leaf arrangement.*—Alternate.
*Margin.*—Entire.
*Displacement.*—Undulated.
*Venation.*—Pinnate.
*Lenticels.*—None.
*Leaf sheathing.*—Prominent on all petioles except those capable of producing flowering buds.

| Leaf size characteristics | Mature | Immature |
|---|---|---|
| Leaf itself: | | |
| (a) Width (1) widest point | 7″ | 3″–3.5″ |
| (2) 1″ from tip | 2″ | 1″ |
| (b) Length | 10″–12″ | 5″–6″ |
| Leaf Petiole: (a) Length | 6″–8″ | 2.5″–4.0″ |
| Leaf, stem and petiole color characteristics, leaf itself: | | |
| (a) Top surface | 7.5GY 4/4 | 7.5Y 5/6 |
| (b) Bottom surface | 2.5GY 4/4 | 2.5YR 4/4 |
| (C) Margin | 2.5R 3/4 | 2.5R 3/4 |
| Leaf Ribs & Veins: | | |
| (a) Top | 7.5GY 5/7 | 10YR 4/4 |
| (b) Bottom | 2.5R 3/4 | 2.5R 3/4 |
| Stem and Petiole | 2.5R 3/4 | 2.5R 3/4 |

I claim:

1. A new and distinct variety of philodendron plant substantially as herein disclosed, characterized as to novelty by its compact growth with better plant volume, improved petiole and stem coloration, high tolerance to unfavorable home conditions, excellent resistance to "shotgun fungus" and bacterial soft rot.

No references cited.

ROBERT E. BAGWILL, Primary Examiner